United States Patent
Angel et al.

(10) Patent No.: US 7,252,816 B1
(45) Date of Patent: Aug. 7, 2007

(54) TOPICAL ACNE VULGAIRS MEDICATION WITH A SUNSCREEN

(75) Inventors: Arturo Angel, Santa Rosa, CA (US); David W. Osborne, Santa Rosa, CA (US); Gordon J. Dow, Santa Rosa, CA (US)

(73) Assignee: Dow Pharmaceutical Sciences, Petaluma, CA (US)

( * ) Notice: Subject to any disclaimer, the term of this patent is extended or adjusted under 35 U.S.C. 154(b) by 0 days.

(21) Appl. No.: 11/393,981

(22) Filed: Mar. 29, 2006

(51) Int. Cl.
*A61Q 17/00* (2006.01)
*A61Q 17/04* (2006.01)
*A61Q 19/04* (2006.01)
*A61K 8/02* (2006.01)

(52) U.S. Cl. .......... 424/59; 424/60; 424/400; 424/401; 514/859

(58) Field of Classification Search ......... 424/59, 424/60, 400, 401; 514/859
See application file for complete search history.

(56) References Cited

U.S. PATENT DOCUMENTS

| | | | |
|---|---|---|---|
| 3,969,516 A * | 7/1976 | Stoughton | 514/24 |
| 4,505,896 A | 3/1985 | Bernstein | |
| 4,671,956 A | 6/1987 | Bouillon | |
| 4,959,213 A | 9/1990 | Brod | |
| 5,017,366 A | 5/1991 | Stiefel | |
| 5,674,912 A | 10/1997 | Martin | |
| 5,679,374 A * | 10/1997 | Fanchon et al. | 424/450 |
| 6,153,176 A * | 11/2000 | Kaleta et al. | 424/60 |
| 6,217,852 B1 | 4/2001 | Gildenberg | |
| 6,355,261 B1 | 3/2002 | Bonda | |
| 2005/0025727 A1 | 2/2005 | Lott | |
| 2005/0089485 A1 | 4/2005 | Stiefel | |
| 2005/0169948 A1 | 8/2005 | Bernstein | |

OTHER PUBLICATIONS

Brisaert M, Investigation on the Photostability of a Tretinoin Lotion and Stabilization with Additives, Int. J. Pharm, 199(1):49-57 (2000) (Abstract only).
Cullen SI, Tretinoin-sunscreen Mixture in the Treatment of Acne Vulgaris, Cutis, 41(4):289-291 (1988) (Abstract only).
Cunliffe WJ, A Double-blind Investigation of the Potential Systemic Absorption of Isotretinoin, when Combined with . . . , Acta Derm Venereol, 81(1):14-17 (2001) (Abstract only).
Eide B, Skin Cancer Awareness and Sun Protection Behaviors in College Students, J. Am. Acad. Dermatol., Abstract P1321 (Mar. 2005).
Kullawanijaya P, Photoprotection, J. Am. Acad. Dermatol., 52:937-958 (2005).
Papageorgiou PP, Chloroxylenol and zinc oxide containing cream (Nels cream) vs. 5% benzoyl peroxide cream in . . . , Clin. Exp. Dermatol., 25(1):16-20 (2000) (Abstract only).
Stiefel Laboratories, Inc., Rosac Cream with Sunscreens, Product Information (2004).
Sirius Laboratories, Inc., Nicomide and Nicomide-T, Product Information (2003).
Tan, JKL, A new formulation containing sunscreen (SPF-15) and 1% Metronidazole (Rosalol Cream) in the treatment of Rosacea, Skin Therapy Letter, 6(8):1-2(2001).
Tan JK, Randomized placebo-controlled trial of metronidazole 1% cream with sunscreen SPF 15 in treatment of rosacea, J Cutan, Med. Surg., 6(6):529-534 (2002) (Abstract only).

* cited by examiner

*Primary Examiner*—Shelley A. Dodson
(74) *Attorney, Agent, or Firm*—Howard Eisenberg, Esq.

(57) ABSTRACT

Increased compliance in the use of topical sunscreens is obtained by combining a topical sunscreen agent in a formulation containing an antibacterial medication such as azelaic acid or an antibiotic.

42 Claims, No Drawings

TOPICAL ACNE VULGAIRS MEDICATION WITH A SUNSCREEN

FIELD OF THE INVENTION

The invention pertains to the field of topically applied medications used to treat acne vulgaris.

BACKGROUND OF THE INVENTION

It is well established that both acute and chronic sun exposure has general detrimental effects to the skin over time. Intervention with the use of sunscreens and sunblocks at a young age is advocated by dermatologists around the world. However compliance is minimal. Avoidance of sun exposure early in life is thought to be particularly important because the carcinogenic effects of the sun are cumulative and are manifested years after the exposure. For children, compliance is dependent primarily on the diligence of the parents. During the teenage years responsibility shifts to the individual, yet teenagers are notoriously noncompliant with the use of sunscreens. In fact the "sun exposed appearance" is regarded as desirable among teenagers generally. Sunscreen use for outdoor activities by adolescents and young adults is highly important for healthy skin, i.e., to minimize the risk of developing skin cancers and to reduce the premature signs of skin aging over time. Therefore, the public health need is great to improve and to facilitate the regular use of sunscreens among adolescents and young adults. It is particularly important to protect the facial area which receives intense and repeated sun exposure.

Recent studies published by the American Academy of Dermatology highlight the lack of compliance of young adults and teenagers in the use of sunscreens. In a study entitled "New American Academy of Dermatology Survey Finds People Aware of the Dangers of the Sun, But Sun Protection Not Necessarily Practiced," Am. Acad. Dermatol. (Apr. 29, 2003), it was reported that, although 79% of surveyed parents and grandparents apply sunscreen to children when they play outdoors, this number drops to only 34% for independent young people under the age of 25. In another study entitled, "New Study Finds High School Students Get Enough UV Exposure on an Average Day to Cause Sunburn", Am. Acad. Dermatol. (Apr. 24, 2002), it was reported that, when high school students between the ages of 12 and 17 were provided with Ultraviolet B dosimeters to wear on their wrists, UVB exposure that occurred during regular daily activities was sufficient to cause sunburn in some students. Moreover, even though UVB exposure was less on cloudy days, the amount of UVB exposure on these days was higher than expected and 80% of the sun's UV rays pass through the clouds. The study also estimated that almost 80% of a person's lifetime sun exposure occurs before the age of 18 Therefore, reducing the exposure of teenagers to harmful rays of the sun is extremely important. In another study entitled "Skin Cancer Awareness and Sun Protection Behaviors in College Students", J. Acad. Dermatol., Abstract P1321, page P107 (March 2005), it was reported that the majority of college students do not use sunscreen on a regular basis. In fact, fully 81% of college students surveyed reported that they never, rarely, or only sometimes use sunscreen.

In a recent article, Kullavanijaya, P, and Lim, H W, J. Am. Acad. Dermatol., 52:937-958 (June 2005), incorporated herein by reference, review the various types of ultraviolet radiation, the harms that these rays can cause upon exposure to skin, and various types of sun protective agents that are applied to protect the skin. As disclosed by Kullavanijaya and Lim, most presently available sunscreen agents are effective primarily in blocking UVB rays and are photolabile, that is they are degraded upon exposure to ultraviolet radiation. Many of the available sunscreens also induce adverse effects such as irritation, allergic contact reactions, photoallergy, and phototoxic effects.

Newer sunscreen agents such as benzene 1,4-di(3-methylidene-10-camphosulfonic acid (MEXORYL SX®, L'Oreal, Clichy, France) (described in U.S. Pat. No. 4,585,597, incorporated herein by reference), drometriazole trisiloxane (MEXORYL XL®, L'Oreal, Clichy, France) (described in U.S. Pat. No. 4,585,597), methylene-bis-benzotriazoyl tetramethylbutylphenol (bisoctrizole, TINOSORB M®, Ciba Specialty Chemicals, Basel, Switzerland) (described in U.S. Pat. Nos. 5,869,030; 5,980,872; and 6,521,217, each of which is incorporated herein by reference), and bis-ethylhexyloxyphenol methoxyphenol triazine (anisotriazine, TINOSORB S®, Ciba Specialty Chemicals) (described in U.S. Pat. Nos. 5,869,030; 5,980,872; and 6,521,217), as well as the inorganic sunscreen agents titanium oxide ($TiO_2$) and zinc oxide (ZnO) are reported by Kullavanijaya and Lim to not share these disadvantages. These agents are broad spectrum UV absorbers, are photostable, and have not been found to cause the adverse effects associated with other sunscreen agents.

Acne vulgaris, often referred to as "acne", is a condition that is distinct from and is not related to acne rosacea. Acne vulgaris is a disorder of the pilosebaceous follicle. Common features of acne vulgaris include increased sebum production, follicular keratinization, colonization by *Propionibacierium acnes*, and localized inflammation.

Treatment for acne vulgaris is typically with one or more of a retinoid, such as tretinoin or isotretinoin, an antibiotic, such as clindamycin or erythromycin, or other medication such as azelaic acid, a sulfonamide, and antibacterials such as benzoyl peroxide. Retinoid compounds increase the sensitivity of skin to the sun and are often inactivated by ultraviolet light. Therefore, retinoid products are recommended to be used at night or together with a sunscreen. Sulfonamides likewise increase the sensitivity of skin to the sun and, therefore, may be combined with a sunscreen. Benzoyl peroxide is highly reactive and degrades upon exposure to the sun. Therefore, benzoyl peroxide may be combined with a physical sunscreen to inhibit this sun-induced degradation. Such problems have not been associated with the use of antibiotics, such as those of the lincomycin family, or with azelaic acid or salicylic acid.

Acne rosacea, often referred to simply as rosacea, is a separate distinct dermatological disorder, which is a chronic inflammatory skin disorder characterized by enhanced epidermal proliferation leading to erythema, typically with flushing, scaling, and thickening of the skin. Rosacea is often exacerbated by exposure to the sun. Therefore, treatment of rosacea often includes the use of sunscreens. In contrast to rosacea, acne vulgaris primarily affects young people, during the teenage years and sunscreens have no known beneficial role in treating acne vulgaris. In fact many sunscreens have been reported to be comedogenic, that is they have the potential to induce comedones which are the primary lesions of acne vulgaris.

The present invention is directed to methods of treating and preventing or inhibiting recurrences of acne vulgaris and addresses the significant need for increasing the compliance in the application of topical sunscreens in individuals suffering from or at risk of developing acne vulgaris, primarily teenagers and other adolescents and young adults. In this way, chronic effects of overexposure to harmful rays of the sun, such as skin cancers, can be greatly reduced.

DESCRIPTION OF THE INVENTION

The present invention addresses a problem that has not been adequately addressed in the prior art and provides a solution to that problem that is distinct from the prior art. The present invention, in its several embodiments, provides a solution to the problem of how to increase compliance in the use of sunscreens, primarily in young people who typically receive a high proportion of their lifetime sun exposure before the age of 20 and who are notoriously non-compliant in the use of sunscreens, especially to the facial areas.

Although the prior art discloses compositions containing certain antibacterial compounds (erythromycin or sulfacetamide) in combination with a sunscreen, the sunscreens in these products are provided either to reduce phototoxic effects of an anti-acne medication or to reduce the sun-induced degradation of the medication. The sunscreens in these compositions were not directed to the problem of reducing facial sun exposure to the individual, except as mentioned to reduce harmful effects of the antibacterial compounds present in the composition. Accordingly, because the prior art is not concerned with the problem of protection from daily sun exposure in the adolescent and young adult populations, the prior art does not disclose sunscreens that are photostable to be combined with these antibacterial compounds.

In contrast, the present invention addresses the problem of lack of compliance in the use of sunscreens, which sunscreens are utilized to protect an individual from the harmful effects due to exposure to the sun. Therefore, certain embodiments utilize a photostable sunscreen agent, as described in more detail below.

The invention, in one embodiment, is a composition for the topical treatment of acne vulgaris. According to this embodiment of the invention, the composition contains one or more sunscreen agents, such as a photostable broad spectrum sunscreen agent, and one or more anti-acne vulgaris chemical agents selected from an antibiotic, like an antibiotic of the lincomycin family, such as lincomycin hydrochloride, lincomycin phosphate, clindamycin phosphate, and clindamycin hydrochloride, azelaic acid, and salicylic acid. Typically, the anti-acne vulgaris agent and the sunscreen agent are dissolved or suspended in a vehicle, such as water, alcohol, or propylene glycol. The composition of the invention is preferably used in single daily or multiple times daily application to the facial area. Preferably, application is once daily, preferably in the morning. The form of the drug product may be a gel, spray, foam, lotion or other dosage form that is cosmetically acceptable for use on the face and which is easily spreadable on the skin. It is preferred to apply the composition of the invention uniformly to all of the acne prone and sun exposed facial and neck areas to optimally treat acne and to reduce the incidence and severity of sunburn and chronic skin damage from solar radiation. The composition of the invention should be spread uniformly on the skin, such as by using the hands and fingers, to completely cover the intended areas of treatment. If the acne medication is used twice daily, the preferred times of application are morning and midday, that is during the hours of sunlight.

The invention is not intended to be used for "spot treatment" of individual acne lesions. Rather, the method of treatment of the invention involves application to broad areas of the face and neck.

In a preferred embodiment, the composition further contains an antioxidant. It has been unexpectedly discovered that combining an antioxidant in a composition containing an antibiotic of the lincomycin family such as clindamycin, and a sunscreen agent, such as a photostable broad spectrum sunscreen like zinc oxide, titanium oxide, or Tinosorb M provides a more stable composition with reduced degradation of the clindamycin during storage. A preferred antioxidant is sodium thiosulfate. Other suitable antioxidants include butylated hydroxyanisole (BHA), butylated hydroxytoluene (BHT), sodium metabisulfite, ascorbic acid, ascorbyl palmitate, thiourea, acetylcysteine, dithiothreitol, cysteine hydrochloride, propyl gallate, and the tocopherols.

The invention, in another embodiment, is a method for topically treating acne vulgaris. Concomitantly, the skin is protected from exposure to the sun. According to this embodiment of the invention, a composition containing one or more sunscreen agents, such as a photostable broad spectrum sunscreen agent, and one or more anti-acne chemical agents, such as azelaic acid or salicylic acid, or an antibiotic like a member of the lincomycin family, such as lincomycin hydrochloride, lincomycin phosphate, clindamycin phosphate, and clindamycin hydrochloride, is applied to the skin of a subject suffering from or at risk of developing skin lesions due to acne vulgaris.

The invention, in another embodiment, is a method for increasing the compliance by individuals such as teenagers and young adults, that is individuals between the ages of 10 and 25, such as between the ages of 13 and 20, and especially those individuals less than 20 years old, in the application of sunscreen, especially to the skin of the face. Adolescents and young adults are often susceptible to, or are suffering from, acne vulgaris and are highly motivated to apply medication faithfully to treat or to combat this condition. By combining a sunscreen, such as a photostable broad spectrum sunscreen agent, in a formulation containing an anti-acne vulgaris medication, such as azelaic acid or salicylic acid, or an antibiotic like an antibiotic of the lincomycin family, such as lincomycin hydrochloride, lincomycin phosphate, clindamycin phosphate, and clindamycin hydrochloride, such individuals will be concomitantly applying a sunscreen, even though such individuals would be less likely do so if the sunscreen were not combined with the anti-acne medication.

As used herein, the term "sunblock" refers to physical sunscreening agents that block exposure of the skin to ultraviolet light. As used herein, the term "sunscreen" or "sunscreen agent" refers to either a physical sunscreen (a sunblocking agent) or a chemical sunscreen. Thus, the term "sunscreen" is broader than the term "sunblock" and encompasses the term "sunblock". As used herein, the term "sunscreen formulation" refers to a formulation that contains a sunscreen and additional components.

As used herein, the terms "photostable sunscreen agent" and "photostable sunscreen formulations" refer to a sunscreen agent or to a formulation containing a sunscreen agent which agent or formulation absorbs ultraviolet radiation at a level that is 50% or higher of the UV absorbance of the agent or formulation prior to irradiation following exposure of a 0.5 ml sample per square centimeter ($cm^2$) in a quartz petri dish of a formulation containing a sunscreen agent to irradiation of 200 watt-h/$m^2$ from a xenon lamp source that correlates to the full spectrum of outdoor sunlight as specified in the International Standard for Outdoor Daylight. D65. The photostable sunscreen formulation may contain a sunscreen agent which is stable as it exists within the formulation but which is unstable inherently. Thus, a formulation is considered to be a photostable sunscreen formulation if it contains a sunscreen that is inherently unstable but is photostable, as defined above, when combined with one or more components present in the formulation.

Sunscreen agents and sunscreen formulations that are suitable for the present invention are photostable as defined above. It is preferred, however, that the photostable sunscreen agents and photostable sunscreen formulations that are used in accordance with the invention be even more stable than that defined above. In a preferred embodiment, the sunscreen agent or sunscreen formulation absorbs ultraviolet radiation at a level that is 75% or higher following the exposure to the xenon lamp source. This level of photostability is referred to herein as "75% photostability." It is most preferred that the sunscreen agents or sunscreen formulations absorb ultraviolet radiation at a level that is 90% or higher following exposure to the xenon lamp source, referred to herein as "90% photostability."

As used herein, a "broad spectrum sunscreen agent" is a chemical compound that absorbs or blocks exposure of both UVB (280 to 320 nm) and UVA (320 to 400 nm). A chemical compound is a broad spectrum sunscreen agent as defined herein if can be formulated to produce an SPF (Sun Protection Factor) of 5 to 10, as determined in accordance with the Testing Procedure specified in 21 C.F.R. Sec. 352.70-352.77 (Subpart D—Testing Procedures), and has a UV-A/UV-B ratio at least 0.75, or if can be formulated to produce an SPF of >10 to 15 and has a UV-A/UV-B ratio at least 0.50, or if it can be formulated to produce an SPF of >15 to 25 and has a UV-A/UV-B ratio at least 0.33, or if it can be formulated to produce an SPF of >25 and has a UV-A/UV-B ratio at least 0.25. The UV-A/UV-B ratio is calculated as the ratio between the areas defined by the UV-A and UV-B extinction capacity, as shown in the following formula wherein A=absorbance and λ=wavelength:

$$\frac{\frac{\int_{320}^{400} A(\lambda) d\lambda}{\int_{320}^{400} d\lambda}}{\frac{\int_{290}^{320} A(\lambda) d\lambda}{\int_{290}^{320} d\lambda}}$$

As used herein, "a broad spectrum sunscreen formulation" is a formulation that absorbs or blocks exposure of both UVB and UVA radiation according to the definition above for a broad spectrum sunscreen agent. Such a formulation may contain one or more broad spectrum sunscreen agents or may contain a multiplicity of sunscreen agents that individually are not broad spectrum agents but, when combined in a formulation, provide a broad spectrum sunscreen function.

Examples of sunscreen agents that are broad spectrum photostable sunscreen agents include inorganic sunscreen agents such as titanium oxide and zinc oxide and tautomeric sunscreen agent compounds such as MEXORYL SX®, MEXORYL XL®, bisoctrizole, and anisotriazine.

As a way to improve the sunscreen usage of teenagers and young adults, this invention embodies a sunscreen, such as a photostable broad spectrum sunscreen, as a second active component along with a topical acne medication. Adolescents and young adults are very commonly afflicted with acne vulgaris and are generally motivated to use preventative topical medications to control acne and maintain their appearance in a positive way. Acne afflicts the face and neck areas primarily and these areas are also the skin areas with the greatest degree of chronic sun exposure.

Additionally patients being treated for acne are at additional risks from sun exposure due to the detrimental effect of sun exposure in combination with commonly used acne medications, both topical and oral. Thus, this invention piggybacks the use of a sunscreen, which is not perceived by teenagers and young adults to be important, on the use of a topical acne medication, which is perceived to be important. Any sunscreen or sun block combined with an antibacterial medication embodies this invention in its broad conception.

In accordance with a preferred embodiment of the invention, the sunscreen is a broad spectrum sunscreen agent or combination of agents. The broad spectrum sunscreen may an inorganic sunscreen agent, such as one or more of zinc oxide (ZnO), titanium oxide (TiO$_2$), or ferric oxide (Fe$_2$O$_3$), which may be in a micronized form. These sunscreen are effective against exposure to UVA (ultraviolet-A) and UVB (ultraviolet-B) light. Alternatively, the sunscreen may be an organic sunscreening agent. An example of an organic sunscreen that is suitable for the invention is a benzotriazole sunscreen, such as methylene bis-benzotriazolyl tetramethylbutyl phenol (MBBT), marketed under the trade name TINOSORB® M (Ciba Specialty Chemicals, Inc., Basel, Switzerland). Other suitable but less preferred organic sunscreening agents include para-aminobenzoic acid (PABA) and derivatives, anthranilates, benzophenones, cinnamates including octylmethoxycinnamate, and salicylates. Other preferred organic sunscreen agents are a camphor derivative such as terephthalylidene dicamphor sulfonic acid, marketed under the trade name MEXORYL® SX (L'Oreal USA, New York N.Y.), and ibenzoylmethanes such as butyl methoxy-dibenzoylmethane (PARSOL® 1789, AVOBENZONE®, Givaudon-Roure Corporation, Totowa, N.J.). A less preferred organic broad spectrum sunscreen agent is oxybenzone, also known as benzophenone, because of recent findings that oxybenzone is associated with a high incidence of skin irritation and is absorbed through the skin into the systemic circulation. The choice and concentration of sunscreens should be made in such a way to achieve a sun protection factor (SPF) of at least about 5, preferably at least about 10, and most preferably about 15 or more.

It is also preferred that the sunscreen agent or that the formulation of the invention containing a sunscreen agent be non-comedogenic. A sunscreen agent or formulation may be determined to be non-comedogenic by the following test.

The comedogenicity test is conducted using semi-occlusive patches on the backs of 20 human volunteers. Subjects exhibiting follicular hyperkeratosis (microcomedones) with a grade 0.5 to 1.0 are suitable for inclusion in the study. Microcomedones are graded on a scale of 0 to 3 with 0=none, 0.5=slight (tiny horny masses), 1=mild (small horny masses involving at least half of the follicles), 2=moderate (moderately sized horny masses over most of the field) and 3=severe (large globoid microcomedones over the entire field) based on follicular biopsy samples from the test area of the back. (Mills, Ohio, The follicular biopsy. In Serup J, Jemec GBE (eds) Handbook of Non-Invasive Methods and the Skin. CRC Press, Baca Raton, La. (1995)). Follicular biopsies are conducted at baseline (up to 45 days prior to study start) and at study end. If a subject has an irritation score of more than 1 at study end, a rest period is given until the initiation score is 1 or less, at which time the final follicular biopsy is performed.

Semi-occlusive patches with 0.1 ml of test product are applied 3 times per week and left in place for 48-72 hours before reapplication to the same site for a 4 week period. Assessments of irritation are made on a 6-point scale with 0=no sign of irritation, 0.5=barely perceptible redness, 1=slight redness, 2=noticeable erythema with slight infiltration, 3=erythema with marked edema, or 4=erythema with edema and blistering. A negative control which is a non-occlusive patch without any test material is applied. The average microdomedone scores for the negative control and the test material are calculated separately by dividing the total of the score by the number of test subjects. A test material is judged to be non-comedogenic if the average score is not more than 0.5 units higher than the negative control.

The acne medication that is useful in the present invention is azelaic acid or salicylic acid, or an antibiotic. The acne medication of the present invention is preferably one that is photostable and that does not increase sensitivity of the skin to sun exposure. As used herein, the terms "photostable" in reference to the acne medication means that the acne medication retains at least 75% of its activity following exposure of the medication in a 0.5 ml sample per square centimeter ($cm^2$) in a quartz petri dish of a formulation containing the acne medication agent to irradiation of 200 watt-hi/$m^2$ from a xenon lamp source that correlates to the full spectrum of outdoor sunlight as specified in the International Standard for Outdoor Daylight. D65.

Preferred antibiotics include macrolide antibiotic including erythromycin, azithromycin, clarithromycin, tilmicosin, and tylosin, and lincomycin-type antibiotics such as clindamycyin hydrochloride, clindamycin phosphate, lincomycin phosphate, or lincomycin hydrochloride. Additional topical anti-acne active ingredients may be contained in the composition of the invention if desired in combination with the salicylic acid, azelaic acid, or antibacterial compound. Such additional topical anti-acne active ingredients include but are not limited to one or more additional antibiotics, salicylic acid, azelaic acid, niacinamide, urea peroxide, and retinoids such as tretinoin, adapalene and tazarotene.

Preferably, the topical acne medication is photostable and does not increase the incidence of adverse reactions to sun exposure, such as occurs commonly with sulfonamides and tetracycline. In topical compositions containing such medications, such as ROSAC® Cream (Stiefel Laboratories, Inc., Coral Gables, Fla.), a sunscreen is included to prevent the deleterious effects of the sun's radiation in combination with a sulfonamide. This is in contrast to the present invention in which a sunscreen is utilized for its effect in preventing damage to an individual caused by exposure to the sun and in which the anti-acne medication in the composition is not degraded by the sun and does not induce adverse effects to an individual when exposed to the sun. Therefore, medications that degrade due to sun exposure or that result in injury to an individual upon exposure to the sun, such as sulfonamides and tetracycline, are expressly excluded from the scope of the present invention.

Additionally, certain skin care compounds, such as benzoyl peroxide, are reactive and degrade due to exposure to sun. For that reason, these compounds may be combined in a composition with a sun filter. See Bouillon, et al, U.S. Pat. No. 4,671,956. Compositions containing benzoyl peroxide are expressly excluded from the scope of the present invention.

The amount and concentration of sunscreen in the composition will vary depending on the particular sunscreen present but is an amount and concentration which is effective to protect an individual from the UV radiation. Similarly, the amount and concentration of the anti-acne medication will vary depending on the particular anti-acne medication in the composition but is an amount that is effective to treat, prevent, or reduce the symptoms of acne vulgaris.

For an optimally effective sunscreen formulation, two or more active sunscreen ingredients may be combined in a composition in order to attain both the breadth of sunscreen protection (UVB and UVA) as well as to achieve sufficient SPF. There are a great many sunscreen ingredients listed in the FDA's OTC monograph of approved sunscreen active ingredients in addition to the sunscreens that are described herein. However, as described above, it is preferred that the composition of the invention contain a broad spectrum sunscreen effective against both UVA and UVB. It is further preferred that the sunscreen is photostable.

Further, there are a multitude of anti-acne ingredients that may be used in the topical treatment and prevention of acne. The anti-acne ingredients, such as salicylic acid, azelaic acid or an antibiotic, may be used singly in the formulation of the invention or in combination with one or more other anti-acne ingredients, such as those listed above. One important factor in utilizing the compositions and methods of the present invention is the selection of anti-acne ingredients and sunscreen ingredients that are compatible with and that are stable within the selected vehicle. There can be physical and chemical incompatibilities wherein one active ingredient adversely affects another or the vehicle. The present invention involves stable formulations in which each active ingredient is compatible within the formulation. This means that the formulation is physically and chemically stable, that is the physical properties of viscosity, odor, and color of the formulation remain substantially unchanged upon storage for a period of 12 months at 25° C. and there is no more than a 10% loss of any active ingredient (sunscreen agent or anti-acne medication) when the formulation is stored for this period of time at this temperature. Making such formulations is described herein, and methods for the manufacture and testing of such formulations for stability are known to those skilled in the art.

Many anti-acne medications and many sunscreens are capable of causing skin irritation. Therefore, if a potentially irritating anti-acne medication is included in the composition of the invention, it is preferred that a non-irritating sunscreen or one with a low irritation potential, such as titanium dioxide, be included. Likewise, if a potentially irritating sunscreen is included in the composition, it is preferred that the anti-acne medication in the composition not be irritating or be only mildly irritating.

An additional benefit of the invention to persons suffering from acne is sun protection, and avoidance of exacerbating the condition when using a product based on this invention. As a result of using the combined product, patients exposed to the sun may be effectively treated by the anti-acne component and be protected from sun exposure.

As previously stated, individuals in the typical acne age group is generally not motivated to use sunscreen products, yet are highly motivated to use products to prevent, treat, and manage their acne. Acne patients under the care of physicians are most commonly given multiple medications as part of their over all treatment regimen. Often, patient compliance is a problem in managing such patients because the young patients do not consider protection from the sun to be of great importance even though they typically place great importance on treating their acne. According to the invention, the sunscreen is combined in the same formulation as the anti-acne medication. This results in an increased compliance for the use of sunscreen products because the patients are motivated to use the anti-acne medication which is in combination with the sunscreen.

The formulation is preferably a semi-solid dosage form, but it may be a liquid including a spray, also. Among the most preferred semi-solid dosage forms, gels are the most preferred, followed by foams, lotions, and creams. Foams, lotions, and creams preferably have a low ratio of oil phase, if present, to water phase. Cosmetic elegance and spreadability of the vehicle are important aspects of this invention in order to obtain patient compliance and uniform and complete application of the sunscreen component to the skin.

By increasing the routine use of sunscreens by adolescents and young adults, multiple health benefits are obtained, including:

An effective method of having adolescents regularly use sunscreens on exposed facial areas, Reduced long-term risk of skin cancer, Minimization of the visible signs of skin aging, Preventing the photo-exacerbation of acne that occurs with sun-exposed acne patients, thus obtaining improved efficacy with the anti-acne component of the combination, and Establishing the habit in these young people of protecting the skin from daily sun exposure and of being responsible for the maintenance of healthy skin.

The invention is further illustrated in the following non-limiting examples that show various embodiments of the invention in various liquid and semisolid dosages forms such as gels, lotions, ointments, and creams. The components of the various embodiments are combined together, such as by mixing, to form the composition. A more detailed procedure for making the composition is provided in the Examples. The compositions of the invention illustrated in the examples above may be made using the procedures described, or by using an alternative procedure known by one skilled in the art.

EXAMPLE 1

A gel composition of the invention may have the following components as shown in Table 1.

TABLE 1

| COMPONENT | Percent (by weight) |
| --- | --- |
| Clindamycin Phosphate | 1.20 |
| Octyl Methoxycinnamate | 7.50 |
| Oxybenzone | 1.00 |
| Edetate Disodium | 0.05 |
| Methylparaben | 0.17 |
| Propylparaben | 0.03 |
| Sodium Docusate (85%) | 1.00 |
| Propylene Glycol | 10.00 |
| Sodium Hydroxide | q.s. pH ≈ 5.5 |
| Carbopol ® 981 (Noveon, Cleveland, OH) | 0.60 |
| Purified Water | q.s. ad 100 |

The gel of Table 1 may be made using the following procedure, or an alternative procedure known by one skilled in the art that is effective to combine the components in a uniform mixture.

Dissolve the disodium edetate in about 90% of the needed water with propeller mixing. Then dissolve the clindamycin phosphate in the first solution again with propeller mixing until the drug is dissolved. After dissolving methylparaben and propylparaben in propylene glycol using heat as needed up to about 80° C. and propeller mixing, add this solution slowly while mixing to the clindamycin solution. Then dissolve the sodium docusate in the clindamycin solution with propeller mixing. Disperse the Carbopol® in the clindamycin solution to form a uniform dispersion. After dissolving the oxybenzone in the octyl methoxycinnamate, slowly pour this sunscreen solution into the Carbopol®dispersion while mixing with a propeller mixer until uniform. After making a 1% sodium hydroxide solution, with continuous mixing add it slowly and stepwise to the Carbopol® dispersion until the designated pH is attained. Add the remaining water and mix into the gel uniformly.

EXAMPLE 2

A gel composition of the invention based on clindamycin as the anti-acne agent with Tinosorb® M and octyl methoxycinnamate as the sunscreens can be made as follows with the components shown in Table 2.

TABLE 2

| COMPONENT | Percent (by weight) |
| --- | --- |
| Clindamycin Phosphate | 1.20 |
| Octyl Methoxycinnamate | 5.00 |
| Tinosorb ® M | 5.00 |
| Edetate Disodium | 0.05 |
| Methylparaben | 0.17 |
| Propylparaben | 0.03 |
| Propylene Glycol | 10.00 |
| Sodium Thiosulfate Pentahydrate | 0.16 |
| Sodium Hydroxide | q.s. pH ≈ 5.5 |
| Carbopol ® 981 | 0.60 |
| Purified Water | q.s. ad 100.00 |

Dissolve the disodium edetate in about 90% of the needed water with propeller mixing. Then dissolve the clindamycin phosphate in the first solution again with propeller mixing until the drug is dissolved. After dissolving methylparaben and propylparaben in propylene glycol using heat as needed up to about 80° C. and propeller mixing, add this solution slowly while mixing to the clindamycin solution. Then dissolve the sodium thiosulfate and sodium docusate in the clindamycin solution with propeller mixing. Disperse the Carbopol® in the clindamycin solution to form a uniform dispersion. Next add Tinosorb® M and octyl methoxycinnamate into the Carbopol® dispersion while mixing with a propeller mixer until uniform. After making a 1% sodium hydroxide Solution, with continuous mixing add it slowly and stepwise to the Carbopol® dispersion until the designated pH is attained. Add the remaining water and mix into the gel uniformly.

The resulting formulation is a cosmetically elegant, low viscosity gel. This composition of the invention has broad protection into the UVA-1 and UVA-2 regions of solar irradiation in addition to the UVB protection.

EXAMPLE 3

The composition of the invention can be made in a variety of pharmaceutical dosage forms that are liquid or semisolid.

The current example is a lotion formulation containing clindamycin as the anti-acne agent and two sunscreens as follows as shown in Table 3.

TABLE 3

| COMPONENT | Percent (by weight) |
| --- | --- |
| Clindamycin Phosphate | 1.20 |
| Octyl Methoxycinnamate | 6.00 |
| Tinosorb ® M | 4.00 |
| Edetate Disodium | 0.05 |
| Sodium Thiosulfate Pentahydrate | 0.10 |
| Benzyl Alcohol | 1.00 |
| Steareth 2 | 0.75 |
| Steareth 21 | 2.25 |
| Propylene Glycol | 10.00 |
| Cetyl Alcohol | 4.00 |
| Isopropyl Myristate | 6.00 |
| Sodium Hydroxide | q.s. pH ≈ 5.5 |
| Carbopol ® 981 | 0.10 |
| Purified Water | q.s. ad 100.00 |

The lotion of Table 3 may be made by first dissolving the disodium edetate, sodium thiosulfate, propylene glycol, and benzyl alcohol in the water with mixing with a propeller mixer. Then dissolve the clindamycin phosphate in the first solution, mixing until the drug is dissolved. Disperse the Carbopol® in the clindamycin solution to form a uniform dispersion. Next add Tinosorb® M into the Carbopol® dispersion while mixing. After making a 1% sodium hydroxide solution, with continuous mixing add it slowly and stepwise to the Carbopol®dispersion until the designated pH is attained, thus completing the water phase. Make the oil phase by combining octyl methoxycinnamate, isopropyl myristate, cetyl alcohol, steareth 2, and steareth 21, all of which is heated to about 65° C. with mixing. Heat the water phase to about 65° C. and add the hot oil phase thereto while mixing with the propeller mixer until the lotion cools to room temperature.

EXAMPLE 4

Following is a cream formulation of the invention containing clindamycin as the anti-acne agent and two sunscreens as follows in Table 4.

TABLE 4

| COMPONENT | Percent (by weight) |
| --- | --- |
| Clindamycin Phosphate | 1.20 |
| Octyl Methoxycinnamate | 6.00 |
| Oxybenzone | 1.00 |
| Edetate Disodium | 0.05 |
| Glyceryl Monostearate | 3.00 |
| Benzyl Alcohol | 1.00 |
| Carbopol ® 1382 (Noveon, Cleveland, OH) | 0.05 |
| Pemulen ® TR-1 (Noveon, Cleveland, OH) | 0.20 |
| Propylene Glycol | 10.00 |
| Cetyl Alcohol | 4.00 |
| Isopropyl Myristate | 8.00 |
| Sodium Hydroxide | q.s. pH ≈ 5.5 |
| Carbopol ® 941 (Noveon, Cleveland, OH) | 0.30 |
| Purified Water | q.s. ad 100.00 |

The cream of this example may be made by first dissolving the disodium edetate, propylene glycol, and benzyl alcohol in the water with mixing with a propeller mixer. Then dissolve the clindamycin phosphate in the first solution, mixing until the drug is dissolved. Disperse the Carbopols® and Pemulen® in the clindamycin solution to form a uniform dispersion. After making a 1% sodium hydroxide solution, with continuous mixing add it slowly and stepwise to the Carbopol® dispersion until the designated pH is attained, thus completing the water phase. Make the oil phase by combining octyl methoxycinnamate, oxybenzone, isopropyl myristate, cetyl alcohol, and glyceryl monostearate, all of which is heated to about 65° C. with mixing. Heat the water phase to about 65° C. and add the hot oil phase thereto while mixing with an appropriate mixer until the cream cools to room temperature.

EXAMPLE 5

This example of the composition of the invention is a solution formulation containing erythromycin base as the anti-acne agent and two sunscreens as follows and as shown in Table 5.

TABLE 5

| COMPONENT | Percent (by weight) |
| --- | --- |
| Erythromycin | 2.00 |
| Octyl Methoxycinnamate | 5.00 |
| Tinosorb ® S | 5.00 |
| Isopropyl Myristate | 1.00 |
| Propylene Glycol | 15.00 |
| Dehydrated Alcohol, USP | q.s. ad 100.00 |

The erythromycin-sunscreen solution is made by first dissolving erythromycin base in the alcohol with mixing. Then each of the remaining components is added and dissolved in the alcohol with mixing, preferably one component at a time.

EXAMPLE 6

A spray dosage form of the composition of the invention is made, for example, by packaging the composition of Example 5 in a bottle fitted with a spray pump closure that can be mechanically actuated by a patient.

EXAMPLE 7

The composition of the invention may be formulated as a gel formulation containing erythromycin base as the anti-acne agent and two sunscreens as follows and as shown in Table 6.

TABLE 6

| COMPONENT | Percent (by weight) |
| --- | --- |
| Erythromycin | 2.00 |
| Octyl Methoxycinnamate | 5.00 |
| Tinosorb ® S | 5.00 |
| Isopropyl Myristate | 1.00 |
| Propylene Glycol | 15.00 |
| Hydroxypropyl Cellulose | 2.00 |
| Dehydrated Alcohol, USP | q.s. ad 100.00 |

The erythromycin-sunscreen gel may be made by dissolving erythromycin base in the alcohol with mixing. Then each of the following ingredients is added and dissolved with propeller mixing, preferably one at a time and in the following order: octyl methoxycinnamate, Tinosorb® S, isopropyl myristate, and propylene glycol. Finally, add the hydroxypropyl cellulose polymer slowly with intense mixing to disperse the polymer followed by side-scrape and countercurrent mixing to make a homogeneous gel.

EXAMPLE 8

The composition of the invention may be formulated as a solution formulation containing salicylic acid as the anti-acne agent and sunscreens as follows and as shown in Table 7.

TABLE 7

| COMPONENT | Percent (by weight) |
| --- | --- |
| Salicylic Acid | 2.00 |
| Octyl Methoxycinnamate | 3.00 |
| Oxybenzone | 1.00 |
| Ethoxydiglycol | 10.00 |
| Polysorbate 20 | 10.00 |
| Cocamide DEA | 5.00 |
| Polyethylene Glycol 300 | 10.00 |
| Tromethamine | q.s. pH ≈ 4.5 |
| Purified Water | q.s. ad 100.00 |

The solution is made by mixing the ethoxydiglycol, polysorbate 20, cocamide DEA, polyethylene glycol 300 and water together, and then dissolving the salicylic acid therein. Then the pH is adjusted by incremental additions of tromethamine (as a 10% solution) to the desired level. Finally the oxybenzone and octyl methoxycinnamate are added and dissolved with propeller mixing.

EXAMPLE 9

The composition of the invention may be formulated as a topical non-aerosol foam with salicylic acid as the active anti-acne drug substance. The solution from example 8 is packaged in a Plastic bottle fitted with a "foamer" pump/closure such as Airspray M3 pump assembly/closure (Airspray International Inc., Pompano Beach, Fla.).

EXAMPLE 10

The composition of the invention may be formulated as an aerosol foam or mousse composition as follows and as shown in Table 8.

TABLE 8

| COMPONENT | Percent (by weight) |
| --- | --- |
| Clindamycin Phosphate | 1.20 |
| Octyl Methoxycinnamate | 2.50 |
| Tinosorb ® S | 2.50 |
| Ethoxydiglycol | 5.00 |
| Polysorbate 20 | 2.00 |
| Lauramine Oxide | 1.0 |
| Cetyl Alcohol | 0.50 |
| Stearyl Alcohol | 0.50 |
| Propylene Glycol | 10.00 |
| Disodium Edetate | 0.05 |
| Methylparaben | 0.17 |
| Propylparaben | 0.03 |
| Sodium Hydroxide | q.s. pH ≈ 5.5 |
| Purified Water | q.s. ad 100.00 |

Heat the water to about 70° C. and with mixing add the propylene glycol and ethoxydiglycol. Add methylparaben and propylparaben to the heated solution and continue to mix until dissolved. Add polysorbate 20 and lauramine oxide with mixing and then clindamycin phosphate, each while continuing to mix the hot solution. In a separate vessel heat octyl methoxycinnamate, Tinosorb® S, cetyl alcohol and stearyl alcohol to about 70° C. and mix. Add the sunscreen mixture to the clindamycin solution slowly with vigorous mixing at elevated temperature. After formation of a homogeneous blend, mix slowly while cooling to about room temperature. Adjust the pH with a 10% solution of sodium hydroxide.

This liquid formulation is packaged into pressurized aerosol containers using, for example, about 95 parts of the formulation and 5 parts of aerosol propellant. One suitable aerosol propellant mixture is one containing about 85% isobutane and 15% propane.

EXAMPLE 11

The composition of the invention may be formulated as a gel composition containing titanium dioxide as one of the sunscreens as follows and as shown in Table 9.

TABLE 9

| COMPONENT | Percent (by weight) |
| --- | --- |
| Clindamycin Phosphate | 1.20 |
| Titanium Dioxide, micronized | 5.00 |
| Edetate Disodium | 0.05 |
| Methylparaben | 0.15 |
| Propylparaben | 0.04 |
| Propylene Glycol | 10.00 |
| Sodium Thiosulfate Pentahydrate | 0.16 |
| Hydroxyethyl Cellulose | 1.00 |
| Purified Water | q.s. ad 100 |

Dissolve the disodium edetate and the sodium thiosulfate in the water with mixing. Then dissolve the clindamycin phosphate in the first solution with propeller mixing until add the drug is dissolved. After dissolving methylparaben and propylparaben in propylene glycol using heat as needed up to about 80° C. and propeller mixing, add this solution slowly while mixing to the clindamycin solution. Add slowly the hydroxyethyl cellulose and disperse it in the clindamycin solution to form a uniform dispersion. Finally add the micronized zinc oxide slowly with mixing to the gel to complete the formulation.

EXAMPLE 12

The composition of Example 1 was tested in an in vitro model in which the sun protection factor (SPF) was estimated to be 14.5. The procedure for determining the in vitro SPF was as follows. The UV spectral irradiance of a 150 watt xenon arc lamp (Solar Light Company, Philadelphia, Pa.) was measured from 290 to 400 nanometers (nm) using an OL 754 Spectromadiometer with a 6 inch integrating sphere (Optronic Laboratories Incorporated, Orlando, Fla.). Approximately 20 mg of test formulation was applied to a roughened 5 cm×5 cm polymethyl methacrylate plate with a known transmittance spectrum (Wendell et al, SOFW Journal, 2001; 127:12-30) and the transmittance spectrum of the sunscreen/substrate combination was measured 5 times at appropriate intervals during irradiation with the solar simulator. The transmitted UV dose was plotted versus the applied UV dose and a least squares curve fit equation was computed for the UV transmission curve (Stanfield, J Cosmetic Science, 2001; 52:412-413). One minimal erythemal dose (MED) equals 6.4 effective mJ/cm². The SPF was computed as the cumulative effective UV dose applied to the sunscreen/substrate at the time when the cumulative transmitted effective UV dose reached 1 MED.

EXAMPLE 13

The composition of Example 2 was tested in an in vitro model in which the sun protection factor (SPF) was estimated to be 27.8. The procedure for determining the in vitro SPF was the same as described in example 12.

EXAMPLE 14

The composition of the invention may be formulated as a gel formulation containing azelaic acid as the anti-acne agent and two sunscreens as shown in Table 10.

TABLE 10

| COMPONENT | Percent (by weight) |
| --- | --- |
| Azelaic Acid | 8.00 |
| Octyl Methoxycinnamate | 4.00 |
| Tinosorb ® S | 5.00 |
| Isopropyl Myristate | 1.00 |
| Propylene Glycol | 5.00 |
| Hydroxypropyl Cellulose | 2.80 |
| Dehydrated Alcohol, USP | q.s. ad 100.00 |

The azelaic acid sunscreen gel may be made by dissolving the azelaic acid in the alcohol with mixing. Then each of the following ingredients is added and dissolved with propeller mixing, preferably one at a time and in the following order: octyl methoxycinnamate, Tinosorb® S, isopropyl myristate, and propylene glycol. Finally, the hydroxypropyl cellulose polymer is added slowly with intense mixing to disperse the polymer followed by side-scrape and countercurrent mixing to make a homogeneous gel.

Various modifications of the above described invention will be evident to those skilled in the art. It is intended that such modifications are included within the scope of the following claims.

The invention claimed is:

1. A photostable, chemically stable, and physically stable formulation for topical application to the skin for treating acne vulgaris and protecting skin from harmful effects of chronic exposure to the sun comprising a vehicle, one or more sunscreen agents dissolved or suspended in the vehicle, which sunscreen agent is selected from the group consisting of titanium dioxide, zinc oxide, bisoctrizole, anisotriazine, para-aminobenzoic acid (PABA) and derivatives, anthranilates, benzophenones, cinnamates, salicylates, camphor derivatives, benzene 1,4-di(3-methylidene-10-camphosulfonic) acid, drometriazole trisiloxane, and dibenzoylmethanes, and an antibiotic medication of the macrolide or lincomycin family that is effective in treating or reducing the signs of acne vulgaris, which antibiotic medication is dissolved or suspended in the vehicle.

2. The formulation of claim 1 wherein the antibiotic medication is clindamycin.

3. The formulation of claim 1 wherein the sunscreen agent is selected from the group consisting of titanium dioxide, zinc oxide, bisoctrizole, and anisotriazine.

4. The formulation of claim 2 wherein the sunscreen agent is selected from the group consisting of titanium dioxide, zinc oxide, bisoctrizole, and anisotriazine.

5. The formulation of claim 1 which further comprises an antioxidant.

6. The formulation of claim 2 which further comprises an antioxidant.

7. The formulation of claim 3 which further comprises an antioxidant.

8. The formulation of claim 4 which further comprises an antioxidant.

9. The formulation of claim 1 wherein the vehicle contains one or more of water, alcohol, or propylene glycol.

10. The formulation of claim 1 which is free of emulsifying agents.

11. The formulation of claim 1 which is a gel.

12. The formulation of claim 11 which contains a carbomer gelling agent.

13. The formulation of claim 1 which contains no other sunscreen agent other than those selected from the group consisting of titanium dioxide, zinc oxide, bisoctrizole, anisotriazine, para-aminobenzoic acid (PABA) and derivatives, anthranilates, benzophenones, cinnamates, salicylates, camphor derivatives, benzene 1,4-di(3-methylidene-10-camphosulfonic) acid, drometriazole trisiloxane, and dibenzoylmethanes.

14. The formulation of claim 1 which is non-comedogenic.

15. A method for making a photostable, chemically stable, and physically stable formulation for topical application to the skin for concomitantly treating acne vulgaris and protecting skin from harmful effects of chronic exposure to the sun comprising dissolving or suspending in a vehicle one or more sunscreen agents selected from the group consisting of titanium dioxide, zinc oxide, bisoctrizole, anisotriazine, para-aminobenzoic acid (PABA) and derivatives, anthranilates, benzophenones, cinnamates, salicylates, camphor derivatives, benzene 1,4-di(3-methylidene-10-camphosulfonic) acid, drometriazole trisiloxane, and dibenzoylmethanes, and dissolving or suspending in the vehicle an antibiotic medication of the macrolide or lincomycin family that is effective in treating or reducing the signs of acne vulgaris.

16. The method of claim 15 wherein the antibiotic medication is clindamycin.

17. The method of claim 15 wherein the sunscreen agent is selected from the group consisting of titanium dioxide, zinc oxide, bisoctrizole, and anisotriazine.

18. The method of claim 16 wherein the sunscreen agent is selected from the group consisting of titanium dioxide, zinc oxide, bisoctrizole, and anisotriazine.

19. The method of claim 15 which further comprises combining an antioxidant in the vehicle.

20. The method of claim 16 which further comprises combining an antioxidant in the vehicle.

21. The method of claim 17 which further comprises combining an antioxidant in the vehicle.

22. The method of claim 18 which further comprises combining an antioxidant in the vehicle.

23. The method of claim 15 wherein the vehicle contains one or more of water, alcohol, or propylene glycol.

24. The method of claim 15 wherein an emulsifying agent is not combined in the vehicle.

25. The method of claim 15 wherein a gelling agent is combined in the vehicle.

26. The method of claim 25 wherein the gelling agent is a carbomer.

27. The method of claim 15 wherein no sunscreen agent other than those selected from the group consisting of titanium dioxide, zinc oxide, bisoctrizole, anisotriazine, para-aminobenzoic acid (PABA) and derivatives, anthranilates, benzophenones, cinnamates, salicylates, camphor derivatives, benzene 1,4-di(3-methylidene-10-camphosulfonic) acid, drometriazole trisiloxane, and dibenzoylmethanes is dissolved or suspended in the vehicle.

28. The method of claim 15 wherein the formulation is non-comedogenic.

29. A method for concomitantly treating, preventing, or reducing the signs of acne vulgaris and protecting skin from ultraviolet radiation comprising applying to the skin a photostable, chemically stable, and physically stable formulation comprising a vehicle, one or more sunscreen agents dissolved or suspended in the vehicle, which sunscreen agent is selected from the group consisting of titanium dioxide, zinc oxide, bisoctrizole, anisotriazine, para-aminobenzoic acid (PABA) and derivatives, anthranilates, benzophenones, cinnamates, salicylates, camphor derivatives, benzene 1,4-di(3-methylidene-10-camphosulfonic) acid, drometriazole trisiloxane, and dibenzoylmethanes, and an antibiotic medication of the macrolide or lincomycin family that is effective in treating or reducing the signs of acne vulgaris, which antibiotic medication is dissolved or suspended in the vehicle.

30. The method of claim 29 wherein the antibiotic medication is clindamycin.

31. The method of claim 29 wherein the sunscreen agent is selected from the group consisting of titanium dioxide, zinc oxide, bisoctrizole, and anisotriazine.

32. The method of claim 30 wherein the sunscreen agent is selected from the group consisting of titanium dioxide, zinc oxide, bisoctrizole, and anisotriazine.

33. The method of claim 29 wherein the formulation further comprises an antioxidant.

34. The method of claim 30 wherein the formulation further comprises an antioxidant.

35. The method of claim 31 wherein the formulation further comprises an antioxidant.

36. The method of claim 32 wherein the formulation further comprises an antioxidant.

37. The method of claim 29 wherein the vehicle contains one or more of water, alcohol, or propylene glycol.

38. The method of claim 29 wherein the formulation is free of emulsifying agents.

39. The method of claim 29 wherein the formulation is a gel.

40. The method of claim 39 wherein the formulation contains a carbomer gelling agent.

41. The method of claim 29 wherein the formulation contains no other sunscreen agent other than those selected from the group consisting of titanium dioxide, zinc oxide, bisoctrizole, anisotriazine, para-aminobenzoic acid (PABA) and derivatives, anthranilates, benzophenones, cinnamates, salicylates, camphor derivatives, benzene 1,4-di(3-methylidene-10-camphosulfonic) acid, drometriazole trisiloxane, and dibenzoylmethanes.

42. The method of claim 29 wherein the formulation is non-comedogenic.

* * * * *